United States Patent
Wang et al.

(10) Patent No.: US 6,838,096 B2
(45) Date of Patent: Jan. 4, 2005

(54) BLACK SOYBEAN POLYSACCHARIDES

(75) Inventors: Sheng-Yuan Wang, deceased, late of Taipai (TW); by Sue-Mei Liu, legal representative, Taipai (TW); Hui-Fen Liao, Taichung (TW); Tsung-Chung Lin, Cheshire, CT (US)

(73) Assignee: Taipei Veterans General Hospital, Taipei (TW)

( * ) Notice: Subject to any disclaimer, the term of this patent is extended or adjusted under 35 U.S.C. 154(b) by 0 days.

(21) Appl. No.: 10/170,159

(22) Filed: Jun. 12, 2002

(65) Prior Publication Data

US 2003/0060449 A1 Mar. 27, 2003

Related U.S. Application Data

(60) Provisional application No. 60/299,495, filed on Jun. 20, 2001.

(51) Int. Cl.$^7$ ........................ A61K 35/78; A61K 31/715
(52) U.S. Cl. ........................ 424/757; 514/54; 514/885
(58) Field of Search ........................ 424/757; 514/54, 514/885

(56) References Cited

U.S. PATENT DOCUMENTS 4,923,809 A * 5/1990 Otsuji et al. ................ 536/123
5,756,318 A * 5/1998 Kosuna ....................... 435/101

FOREIGN PATENT DOCUMENTS

EP  1 096 022 A1  5/2001  ........... C12P/19/04

OTHER PUBLICATIONS

Long et al. 1999. Shipin Kexue (Beijing). vol. 20, No. 9, pp. 9–12, see English abstract.*

Database CAPLUS, CAS (Columbia, Ohio), AN 1999:682644, Long et al. "Study on inhibitory effect of black soybean pigment and polysaccharide on whole blood chemiluminescence and active oxygen". Abstract, Shipin Kexue (Beijing), 1999 20(9), 9–12.

* cited by examiner

Primary Examiner—Christopher R. Tate
(74) Attorney, Agent, or Firm—Fish & Richardson P.C.

(57) ABSTRACT

A nutraceutical composition containing 0.01–99% by weight polysaccharides enriched from an extract of beans of *Glycine max* (L.) Merr. Also disclosed are a method of enriching polysaccharides from pulverized beans of *Glycine max* (L.) Merr.; a polysaccharide having a backbone of α-(1,6)-linked glucose residues, and one or more galactose or mannose residues are bonded to the C-3 or C-4 position of one or more of the glucose residues by a (1,3)- or a (1,4)-linkage; and a method of treating a subject with such polysaccharides to increase blood cell counts.

5 Claims, No Drawings

BLACK SOYBEAN POLYSACCHARIDES

CROSS REFERENCE TO RELATED APPLICATION

Pursuant to 35 U.S.C. §119(e), this application claims the benefit of prior U.S. provisional application No. 60/299,495, filed Jun. 20, 2001.

BACKGROUND OF THE INVENTION

According to recent reports, ingredients from soybeans, *Glycine max* (L.) Merr., are capable of modulating immune responses, preventing carcinogenesis, and inhibiting tumor growth. See, e.g., Zhang et al., *Nutr. Cancer*, 1997, 29: 24–28; Zhou et al., *J. Nutr.*, 1999, 129: 1628–635; Benjamin et al., *Brazilian J. Med. Biol. Res.*, 1997, 30: 873–881; Rao et al., *J. Nutr.*, 1995, 125 (suppl 3): S717–S724; and Meydani et al., *J. Am. Colle. Nutr.*, 1991, 10: 406–428.

Black soybean (*Glycine max* (L.) Merr.) is a soybean cultivar with a black seed coat. It has been used for at least hundreds of years in traditional Chinese medicine.

It has also been reported that herbal prescriptions containing black soybeans and other herbs increased the number of white blood cells in leukopenic patients. See Wang, *Trad. Chi. Med. Res.*, 1992, 5: 35–36. However, it is not clear whether any compound or compounds in black soybeans account, fully or in part, for the therapeutic effect.

SUMMARY OF THE INVENTION

The present invention is based on the discovery that polysaccharides purified from soybeans in general, and black soybeans in particular, possess useful biological activities.

Accordingly, one aspect of this invention relates to a nutraceutical composition, which can be a soft drink, milk, a snack bar, juice, a dietary supplement, or a botanical drug. The nutraceutical composition contains 0.01–99% by weight (e.g., 0.01–1% as in a soft drink or milk; or 1–99% as in a dietary supplement or botanical drug) polysaccharides enriched from an extract of soybeans or black soybeans. The content of the polysaccharides in the composition (i.e., 0.01–99% by weight) can be determined by methods well known in the art. Such polysaccharides are able to increase the number of blood cells, stimulate the production of cytokines, and enhance immunity. In other words, a polysaccharide-enriched extract of soybeans, especially black soybean, is used as an active ingredient in the nutraceutical composition of this invention. The polysaccharides can be either protein free or associated with protein.

Another aspect of this invention relates to a polysaccharide having a backbone of α-(1,6)-linked glucose residues, and one or more (e.g., 4 or 5) glucose, galactose, or mannose residues bonded to the C-3 or C-4 position of one or more of the glucose residues by a (1,3)- or a (1,4)-linkage, e.g., one or more residues at some C-4 positions of a backbone glucose residue and/or one or more residues at the C-3 position of the same or another backbone glucose residue. The molar percentage of the residues can be 5% galactose, 6% mannose, and 89% glucose (±20%). The molecular weight of the polysaccharide is higher than 80 KDal, e.g., in the range of 300 to 600 KDal.

A further aspect of this invention relates to a method of enriching polysaccharides from soybeans or black soybeans. These polysaccharides generally have a high molecular weight, i.e., higher than 80 KDal (e.g., 300 to 600 kDal). The method includes the steps of soaking pulverized beans in water or a mixture of water and an organic solvent (e.g., ethanol) to dissolve the polysaccharides (with or without prior removal of low polarity contents by soaking the pulverized beans in an organic solvent or by mechanical pressure); and removing the insoluble contents by filtering or centrifugation and collecting the supernatant. The polysaccharides contained in the supernatant can be obtained by concentrating the supernatant solution by evaporation or by precipitating with a sufficient amount of ethanol followed by filtering or centrifugation. Optionally, a sufficient amount of precipitation enhancing agent can be added to the solution for precipitating the majority of lipid and protein contents, before the insoluble contents are removed. A precipitation enhancing agent is a compound or composition which can induce precipitation of dissolved components. Examples of a precipitation enhancing agent for lipids or proteins include acids (e.g., acetic acid and hydrochloride), sodium salts (e.g., sodium chloride), calcium salts (e.g., calcium sulfate and calcium chloride), magnesium salts (e.g., magnesium chloride), and ammonium salts (e.g., ammonium sulfate). The supernatant can also be optionally dialyzed (e.g., by pressure dialysis or ultra-filtration) and concurrently concentrated to remove compounds smaller than the polysaccharides prior to collecting the polysaccharides. Alternatively, ethanol can be added to the supernatant in increments to the volume percentage of 10–80% (e.g., 10–20%, 20–30%, 30–40%, 40–50%, or 50–60%) to precipitate the high molecular weight polysaccharides.

The highly enriched high molecular weight polysaccharides can also be treated with a protease and then dialyzed or precipitated with ethanol again for removal of the protease and peptides.

The term "high molecular weight polysaccharides" used throughout this disclosure refers to polysaccharides having a molecular weight higher than 80 KDal (e.g., 300 to 600 KDal), which can be extracted from soybeans or black soybeans. Such polysaccharides can go through modifications, e.g., by ultrasound fragmentation or by enzymatic digestion to reduce its molecular weight.

This invention also includes a method of increasing in a subject the number of blood cells, which include erythrocytes, megakaryocytes, and especially leukocytes (such as myeloid-lineage leukocytes, e.g., neutrophiles, monocytes, granulocytes, and eosinophils). More specifically, the subject is treated with polysaccharides prepared (i.e., enriched or purified) from an extract of pulverized soybeans or black. The polysaccharides can have a high molecular weight (i.e., higher than 80 KDal, e.g., 300–600 KDal) or a low molecular weight (i.e., lower than 80 KDal), or can be a combination of those of a high molecular weight and those of a low molecular weight. The polysaccharides can be directly administered to the subject. Alternatively, one can take an ex vivo approach as follows: Peripheral blood cells (which consist of mature blood cells, as well as progenitor cells including stem cells), bone marrow cells, or their combination can be collected from the subject, incubated with the polysaccharides in a medium, and then returned to the subject.

The polysaccharides prepared from soybeans or black soybeans can also be used to activate cellular immunity by increasing TNF α and other cytokine levels, and can enhance a subject's immunity in preventing or treating cancer. It can also be used to improve the health of a patient infected by disease causing agents such as HIV, by increasing the blood cell number and boosting the immune system.

Also within the scope of this invention is a method of obtaining a cytokine (such as TNF α, INF γ, interleukin-3, interleukin-6, interleukin-17, granulocyte-colony stimulating factor, monocyte-colony stimulating factor, or granulo-monocyte-colony stimulating factor). The method includes use of polysaccharides prepared from soybeans or black soybeans. For instance, cytokine-producing cells collected from a mammalian animal can be incubated in a medium containing polysaccharides prepared from soybeans or black soybeans for production of cytokines. A cytokine thus obtained is then isolated from the medium. Alternatively, the polysaccharides can be administered to a mammalian animal to stimulate the production of a cytokine. The cytokine can then be isolated from the blood of the animal.

The invention further relates to a method of preventing or treating cancer in a subject. The method includes administering to a subject in need thereof polysaccharides prepared from an extract of beans of *Glycine max* (L.) Merr. or a polysaccharide having a backbone of α-(1,6)-linked D-glucose residues and side-chains having one or more residues of galactose, mannose, or glucose. The cancer can be either leukemia or a solid tumor.

Also contemplated within this invention are pharmaceutical compositions containing polysaccharides and pharmaceutically acceptable carriers; and a method of increasing the number of blood cells in a subject by treating the subject, in vivo or ex vivo, with the pharmaceutical compositions; and a method of increase the immunity of a subject in preventing or treating cancer or infectious diseases, with the pharmaceutical compositions. The polysaccharides contained in the compositions can be those enriched from soybeans or black soybeans, which have a molecular weight of higher than 80 KDal (e.g., 300–600 KDal) or lower than 80 KDal; or those each having a backbone of α-(1,6)-linked D-glucose residues and side-chains having one or more residues of galactose, mannose, or glucose, Other features, objects, and advantages of the invention will be apparent from the following description and from the claims.

DETAILED DESCRIPTION OF THE INVENTION

Various embodiments of this invention are based on the observations that polysaccharides purified from soybeans or black soybeans stimulates the production of cytokines, increase blood cell numbers, and enhance immunity.

The polysaccharides can be extracted from pulverized black soybeans of various sources and enriched by the following method. Pulverized black soybeans are optionally soaked in an organic solvent (e.g., ethanol) or mechanically pressured to remove low polarity contents such as fatty acids. The organic solvent insoluble portion is then soaked in water or an aqueous solution at an elevated temperature for an adequate length of time (e.g., 10 minutes at 100° C. or 8 hours at 60° C.) to extract the polysaccharides. The extract is collected (e.g., by filtration), and optionally treated with reagents such as calcium sulfate to precipitate low polarity contents and proteins. The precipitates can then be removed by centrifugation or filtering. The polysaccharide solution is then optionally enriched and condensed (e.g., by pressure dialysis or ultrafitration or by precipitate the polysaccharides with ethanol, e.g., in the amount of 10–80% by volume), and then, optionally, dried (or freeze-dried) to obtain a polysaccharide preparation. The condensed extract can be treated with a protease (e.g., protease K) and then dialyzed or precipitated again to remove the protease and small peptides. If desired, the polysaccharide preparation can be further enriched or even purified by gel filtration or other suitable methods. The average molecular weight of a polysaccharide or polysaccharide mixture that was potent in stimulating blood cell proliferation and enhancing host immune system, is approximately 480 KDal, as determined by gel filtration chromatography. One content in these polysaccharides is a polysaccharide having a backbone of α-(1,6)-linked glucose residues, and one or more (e.g., 4 or 5) glucose, galactose, or mannose residues bonded to the C-3 or C-4 position of one or more of the glucose residues by a (1,3)- or a (1,4)-linkage, e.g., one or more residues at some C-4 positions of a backbone glucose residue and/or one or more residues at the C-3 position of the same or another backbone glucose residue. The molar percentage of the residues can be 5% galactose, 6% mannose, and 89% glucose (±20%).

The amount of polysaccharides is determined by a phenol-sulfuric acid total carbohydrate determination assay, or any analogous methods. See, e.g., Fox et al., *Anal. Biochem.*, 1991, 195: 93–96. For instance, a mixture of the polysaccharide and phenol is added to the wells of a microtiter plate and shaken at a low speed, and cooled with ice. Concentrated sulfuric acid is then added into each well. The plate is again shaken at a low speed, incubated at an elevated temperature, and cooled. The absorbance at 492 nm is measured to determine the amount of monosaccharide (hydrolyzed from the polysaccharide), using maltose or D-glucose as the standard.

A polysaccharide preparation thus obtained can be used to formulate a nutraceutical composition for treating (including preventing or ameliorating the symptoms of) a disorder related to low cytokine levels or low blood cell counts (especially leukocyte counts), e.g., cancer patients after chemotherapy. The nutraceutical composition can be a dietary supplement (e.g., a capsule or tablet, or placed in a mini-bag), a food product (e.g., a soft drink, milk, juice, or confectionary, or placed in a herbal tea-bag), or a botanical drug. The botanical drug can be in a form suitable for oral use, such as a tablet, a hard or soft capsule, an aqueous, or a syrup; or in a form suitable for parenteral use, such as an aqueous propylene glycol solution, or a buffered aqueous solution. The amount of the active ingredient in the nutraceutical composition depends to a large extent on a subject's specific need. The amount will also vary, as recognized by those skilled in the art, depending on administration route, and possible co-usage of other agents that also can stimulate production of cytokines or increase blood cell numbers.

Partially or highly purified polysaccharides in an effective amount can be formulated with a pharmaceutically acceptable carrier into a pharmaceutical composition for treating the above-mentioned disorders. "An effective amount" refers to the amount of the polysaccharides which is required to confer therapeutic effect on the treated subject. Effective doses will vary, as recognized by those skilled in the art, depending on the route of administration, the excipient usage, and the optional co-usage with other therapeutic treatments. Examples of pharmaceutically acceptable carriers include colloidal silicon dioxide, magnesium stearate, cellulose, sodium lauryl sulfate, and D&C Yellow #10.

The polysaccharides can be formulated into dosage forms for different administration routes utilizing conventional methods. For example, it can be formulated in a capsule, a gel seal, or a tablet for oral administration. Capsules may contain any standard pharmaceutically acceptable materials such as gelatin or cellulose. Tablets may be formulated in accordance with conventional procedures by compressing mixtures of the polysaccharide with a solid carrier and a lubricant. Examples of a suitable solid carrier include starch and sugar bentonite. The polysaccharide can also be administered in the form of a hard shell tablet or a capsule containing a binder, e.g., lactose or mannitol, a conventional filler, and a tableting agent. The pharmaceutical composition may be administered via a parenteral route, e.g., topically, intraperitoneally, and intravenously. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic compound.

Also within the scope of this invention is use of polysaccharides prepared from black soybeans for treating the disorders mentioned above or for manufacture of a medicament for treating such disorders.

An in vitro assay can be used to evaluate the efficacy of a nutraceutical or pharmaceutical composition of this invention in stimulating the production of cytokines (e.g., by an enzyme-linked immunosorbent assay (ELISA)) or increasing the number of blood progenitor cells (e.g., by a granulomonocyte colony forming unit (CFU-GM) assay). For instance, cytokine-producing cells (e.g., spleen cells or mononuclear cells) can be incubated in a medium in the presence of a composition of this invention for elevated cytokine production. The amounts of the cytokines thus produced in the medium can then be measured (e.g., by ELISA kits). The spleen cell medium, which contains cytokines, can be incubated with bone marrow cells to increase blood cell numbers. The increase in the number of progenitor cell can be measured by counting the total number of colonies in a CFU assay.

The efficacy of a composition of this invention which has been preliminarily screened (in vitro) can be confirmed by an in vivo assay. For example, mice can be fed with a polysaccharide-containing composition with their blood cell numbers or cytokine levels determined at intervals. Different dosages and administration can be tested. Based on the results, an appropriate dosage range and administration route can be determined. The information obtained from animal models can be based on to design clinical studies.

Without further elaboration, it is believed that one skilled in the art can, based on the description herein, utilize the present invention to its fullest extent. The following specific examples, which describe preparation and tests of polysaccharide from black soybeans, are therefore to be construed as merely illustrative, and not limitative of the remainder of the disclosure in any way whatsoever. Thus, although the examples below describe isolation and use of polysaccharide prepared from a strain of black soybean, polysaccharides prepared from other strains of black soybean or soybean (which might have structures somewhat different from that described in Example 1 below) and their uses are also within the scope of this invention. All publications cited herein are hereby incorporated by reference in their entirety.

EXAMPLE 1

Isolation and Structural Characterization of Polysaccharides from Black Soybeans Beans from a strain of *Glycine max* (L.) Merr. (dark purple-black coat and green cotyledons, obtained from Tainan District Agricultural Improvement Station, Taiwan, ROC) were shredded and soaked in an organic solvent to remove low polarity contents. The shredded beans were then soaked in water. After centrifugation, the water extract, i.e., supernatant, was purified by liquid chromatography, subsequently, with a Sephadex LH-20 column (Amersham Pharmacia Biotech., Little Chalfont, Buckinghamshire, England) and a Fractogel TSK HW-55F column (Merck, Darmstad, FRG). The purified water extract was treated with protease K (50 mg/ml; Sigma Co., Saint Louis, Mo.) at 37° C. for 1 hour. Finally, the protease-treated water extract was further purified by gel filtration using a Sephacryl S-400 column (Amersham Pharmacia Biotech) and dried by lyophylization to give the polysaccharide. The results from S-400 column suggested that the major polysaccharide has a molecular weight of approximately 480 KDal.

The molecular weight of the polysaccharides was determined by using standard dextran (Amersham Pharmacia Biotech.) for calibration. See, e.g., Liao et al., *Anticancer Drugs*, 2001, 12 (10):841–846; Hara et al., *Carbohydr. Res.*, 1982, 110: 77–87; and Ukai et al., *Carbohydr. Res.*, 1982, 101: 109–116. Total carbohydrate determination was performed by a phenol-sulfuric acid colorimeric assay using glucose as a standard. See Fox et al., *Anal. Biochem.*, 1991, 195: 93–96. Its monosaccharide composition was determined after it was hydrolyzed with 2.0 N trifluoroacetic acid at 100° C. for 6 hours, and then purified by ion exchange with a Dionex DX-500 Chromatography system with a carboPac™ MA-1 column. See, e.g., Hardy et al., *Anal. Biochem.*, 1988, 170: 54–62. The composition of the major polysaccharide and linkages between monosaccharides was also determined by using $^1$H- and $^{13}$C-NMR spectroscopy or gas liquid chromatography-mass on an HP 5973 MSD with HP 6890 series GC system (HP company, Wilmington, Del.). The specific rotation of the polysaccharide can be measured on a JASCO DIP-370 digital polarimeter (JASCO Corp., Japan) in water at 24° C. with a sodium lamp at 589 nm.

The major polysaccharide had a specific rotation of $[\alpha]_D+$ 122.2°, c=0.45, in water. Spectrum results suggest that the polysaccharide is essentially composed of a backbone of α-(1,6)-linked D-glucose residues with galactose, mannose, or glucose residues substituted at C-3 or C-4 positions by branches of (1,3)- or (1,4)-linkage The molar percentages of the residues are 5% galactose, 6% mannose, and 89% glucose (±20%).

The polysaccharides (with the above mentioned polysaccharide as its major component) thus obtained, or obtained using similar methods, were stored and used in experiments described in the following Examples.

EXAMPLE 2

Effect of Polysaccharides on Cytokine Production

Spleens were removed from ICR mice (8–10 weeks of age, 20–25 g) bred under specific pathogen-free conditions, homogenated to single cells, and dispersed into a suspension using a 1-mm metal sieve. The spleen cells ($1\times10^7$ cells/mL) were then incubated in a 10% fetal calf serum (FCS)-containing RPMI 1640 medium with protease treated and Sephacry S-400 column purified polysaccharides at various concentrations (e.g. 0, 12.5, 25, 50 and 100 μg/ml) at 37° C. in a fully humidified atmosphere of 5% $CO_2$ in air. After 72 hours, the spleen cell-conditioned media (SCMs) were collected, sterilized, and then stored as 1-mL aliquots at −70° C. until use.

Measurement of the cytokines produced in the SCMs (i.e., interleukin-3, interleukin-6, interleukin-17, granulocyte-colony stimulating factor, monocyte-colony stimulating factor, and granulo-monocyte-colony stimulating factor) was performed with ELISA kits (R&D Systems, Minneapolis, Minn.) while using a SCM containing non-treated spleen cells as a control. See, e.g., Liao et al., *Anticancer Drugs*, 2001, 12 (10):841–846; and *Current Protocols in Molecular Biology*, Chapter 11, Academic Press, John, Wiley and Sons, Inc., 1998.

After 3-days of stimulation, the amounts of IL-17, GM-CSF, G-CSF and IL-6 in PSBS-SCMs were dramatically increased.

EXAMPLE 3
Effect of Polysaccharides on Colony Forming Units
a) Effects on Granulocyte-macrophage Colony-forming Unit (CFU-GM)

CFU-GM assay using a soft-agar culture method was performed as described in Wang et al., Exp. Hematol., 1996, 24: 437. Bone marrow cells collected from ICR mice were resuspended in RPMI 1640 medium supplemented with 10% FCS and cultured at 37° C. for 90 minutes in a humidified 5% $CO_2$ incubator. The non-adherent bone marrow cells ($1\times10^5$ cells/mL) were then plated in a 1-mL layer of 0.3% agar (Sigma) in McCoys' 5A medium supplemented with 15% FCS, essential and non-essential amino acids, vitamin C and sodium pyruvate. Various 20% (v/v) SCMs or polysaccharides alone were added while plating with the same final cell concentrations. After incubation for 7 days, the number of colonies on each plate was counted using an inverted microscope (Olympus, Melville, N.Y.). The morphology of colony was determined in situ after fixation with 5% glutaraldehyde, and dehydration with methanol, and staining with Harris' hematoxylin. See, e.g., Wang et al., Exp. Hematol., 1992, 20:552.

The results show that the polysaccharide treatment significantly increased the colony formation of cultured bone marrow cells in the treated SCMs. Morphological analysis indicated that four types of colonies, i.e., granulocyte, monocyte/macrophage, granulo-monocyte, and eosinophil, were induced by the polysacchraide treatment.

b) Effect on Multipotential (CFU-GEMM) and Erythroid (BFU-E) Colony-forming Units The colony assay for CFU-GEMM and BFU-E were carried out according to the procedure as described by Wang et al. in the Proceedings of the 1990 Science, Engineering and Technology. Houston: AACP, Hsieh ed., 1990, (S1): 10; and in Wang et al., Blood, 1985, 65: 1181. Specifically, $5\times10^4$ bone marrow cells were plated in 35 mm culture dishes containing a 1 mL mixture of 1% methylcellulose in Iscove's modified Dulbecco's medium (StemCell Technologies, Vanconver, Canada), 30% FCS, 1% bovine serum albumin, $10^{-4}$ M 2-mercaptoethanol, 2 mM L-glutamine, 1 unit erythropoietin (EPO; Connaught Laboratories Ltd, Willowdale, Ontario, Canada), and 20% various SCMs. The dishes were incubated at 37° C. in a humidified atmosphere flushed with 5% $CO_2$ in the air for 7 days. After the incubation, colonies were identified and scored with an inverted microscope. CFU-GEMM showed mixed colonies containing granulocyte (G), erythrocyte (E), monocyte/macrophage (M) and megakaryocyte (M), while BFU-E showed multicentric (Burst) erythroid colonies with a red or pink color.

The results indicate that the polysaccharide treatment markedly augmented the CFU-GEMM and BFU-E colony formation in SCMs in a dose-dependent manner.

EXAMPLE 4
Effect of Polysaccharides on Myelopoiesis in Mice

To examine the effect of the polysaccharides on irradiated mice, twenty ICR mice were divided into the following four groups (5 mice per group): control, treated with the polysaccharides alone, total body irradiation (TBI) alone, and TBI and polysaccharide administration. The entire body of each mouse was irradiated in a single fraction with 8 Gy (6 MV photon beam) using a linear accelerator (Clinac® 1800, Varian Associates, Inc., CA, USA, dose rate 2.4 Gy/min) on day 0. Oral administration of polysaccharides (400 mg/kg) started 6 hours after TBI from day 0 to 4. In the control group, the mice received normal saline orally. Peripheral blood was collected from the orbital sinus on days 0, 2, 4, 6, 8, 10, 12, 14 and 16, and leukocytes were counted using a Coulter counter. In addition, mouse body weight was measured every other day during the experimental period. On day 17, the mice were sacrificed and bone mineral contents (BMCs) were removed for colony-forming assay. Myeloid colony formation (CFU-GM) was assessed by the method described above.

5-fluorouracil (5-FU) was interperitoneally injected with a single dose of 150 mg/kg to the ICR mice. Six hours later, 400 mg/kg of polysaccharide was given orally for 5 consecutive days. The mice were sacrificed on day 11 and BMCs were collected for colony-forming assay. The results show that in these two in vivo protocols, the baseline leukocyte counts of ICR mice in untreated control and polysaccharide-treated groups were similar. Both radiation and 5-FU treatment caused apparent myelosuppression. The number of leukocytes significantly decreased after TBI and 5-FU treatment. Continuous administration of the polysaccharides for 5 days (from day 0 to 4) not only reduced the degree of leukopenia caused by TBI and 5-FU, but also shortened the recovery time of leukocytes counts. After TBI and 5-FU treatment, the CFU-GM colony numbers were greatly diminished (33±6 and 41±5 colonies, respectively). Administration of the polysaccharides could reconstitute myelopoiesis in irradiated and 5-FU-treated mice, and the number of CFU-GM increased about 2.0-fold (TBI) and 1.8-fold (5-FU) as compared with the TBI and 5-FU alone group.

EXAMPLE 5
Effect of Polysaccharides on Leukemic Cell Line U937

The human myeloid leukemic cell line, U937, obtained from the American Type Culture Collection (Rockville, Md.), was used in this study to illustrate the anticancer property of the polysaccharides. The U937 cells were cultured in RPMI 1640 medium supplemented with 10% FCS and maintained at 37° C. in a humidified 5% $CO_2$ incubator. $1\times10^5$ cells/ml were cultured in the presence or absence of 30% (v/v) of normal MNC-CM (N-MNC-CM), PSBS (25–400 $\mu$g/ml)-MNC-CMs or PSBS (25–400 $\mu$g/ml) alone. After incubation for 5 days,the cells were collected by gently rubbing the dishes with a rubber policeman (Bellco Glass, Vineland, N.J.) and the number of viable cells were was counted using the trypan blue dye exclusion test.

The results indicated that the proliferation of U937 cells was significantly inhibited by PSBS-MNC-CM. However, no significantt inhibition was observed in normal MNC-CM or PSBS (up to 400 microg/ml) alone.

After 5 days of various treatments, the cells were collected and cytocentrifuged onto a microscope slide using a Cytospin (Shandon Southern Instrument Inc.), stained with Wright's stain, and observed under an inverted microscope (Olympus) with a magnification of 1000×. The cellular morphology was classified into three stages: immature blasts, intermediates, and mature monocytes or macrophages.

The results showed that PSBS-MNC-CM triggered immature blast cells to differentiate into mature monocytes and macrophages. The percentage of blast cells decreased dramatically from 98.7±0.9% (untreated control) to 2.3±1.5% (MNC-CM prepared with 400 microg/ml of PSBS). By contrast, the percentage of monocytes plus macrophages increased from 0±0% (untreated control) to 83.0±4.0% (PSBS-MNC-CM).

EXAMPLE 6
Effect of Polysaccharides on Promoting Myelopoietic Activity

BALB/c mice (6–10 weeks old, 20±5 g) were obtained and kept in specific pathogen-free conditions with a controlled temperature and humidity, under a 12-h light/dark cycle, and given free access to food and water. All experiments were performed in accordance with the guidelines provided in the NIH *Guide for the Care and Use of Laboratory Animals* (DHHS publication No. NIH 85-23, revised 1996). CT26 murine colon adenocarcinoma and BALB/c syngenic were maintained in RPMI 1640 medium (Life technology, Grand Island, N.Y.) supplemented with 10% heat-inactivated FCS (HyClone, Logan, Utah) and 2 mM L-glutamine (Sigma, St. Louis, Mo.), and cultured at 37° C. in a humidified atmosphere containing 5% $CO_2$. These cells were subcutaneously implanted into left flank of BALB/c mice.

For non-tumor implanted experiments, 5-FU (150 mg/kg body weight) was intraperitoneally (i.p.) injected into BALB/c mice on day 0, and PSBS (100 or 400 mg/kg body weight) was given by oral or interperitoneal administration daily once for 5 consecutive days 6 h after 5-FU injection. Mice in control group received normal saline at the same time. While in tumor-implanted model, $1 \times 10^6$ CT26 tumor cells in PBS per mouse was s.c. injected in the left flank of mice. After 10 days, tumor grew up to about 0.5 cm$^2$ in size, and then mice were divided into three groups (5 mice per group) including control, 5-FU (150 mg/kg, i.p.) alone and 5-FU plus polysaccharide (400 mg/kg, p.o.). Then, the drug treatment protocol was the same as previous method for tumor free experiments.

The results show that the 5-FU treatment significantly reduced the number of leukocytes in mice with or without tumor implantation. Combined treatment of PSBS for 5 days not only reduced the severity of the nadir value of leukocytes count caused by 5-FU myelosuppression, but also increased the recovery rate of the leukocyte counts after nadir. The polysaccharide treatment also increased the amounts of cytokines in mice with tumor implantation and 5-FU treatment.

EXAMPLE 7
Effect of Polysaccharides on Reducing Tumor Growth

Approximately $1 \times 10^6$ CT26 tumor cells in PBS per mouse was subcutanesously injected in the left flank of BALB/c mice on day 0. The mice were divided and treated as the following four groups: (1) Control, treated with PBS four days per week, started from day 1; (2) polysaccharides alone, 400 mg/kg, p.o., four days per week, started from day 1; (3) 5-FU alone, 15 mg/kg, interperitoneally., once per week; started on day 11; (4) a combination of polysaccharides started on day 1 and 5-FU started on day 11. Peripheral blood was collected from the orbital sinus for leukocyte counts by using heparinized capillary tubes and Coulter counter. The mice body weights and tumor sizes were measured twice per week during the experimental period, and the tumor size was measured with calipers and calculated using the equation: (Length/2)(Width/2)$\pi$. See, e.g., Wang et al., *Anti-Cancer Drug Des.*, 1998, 13: 779.

The results show that the polysaccharide treatment significantly reduced the tumor sizes. After day 11, the tumor sizes of group (2) were measured to be significantly smaller than that of group (1), and after day 20, the tumor sizes of group (4) were measured to be significantly smaller than that of group (3).

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Accordingly, other embodiments are also within the claims.

What is claimed is:

1. A method of increasing the number of blood cells in a subject, comprising administering to a subject in need thereof a polysaccharide-enriched extract prepared from beans of *Glycine max* (L.) Merr, wherein the extract contains a polysaccharide having a backbone of $\alpha$-(1,6)-linked D-glucose residues.

2. The method of claim 1, wherein the blood cells are myeloid-lineaged.

3. The method of claim 2, wherein the myeloid-lineage cells are leukocytes.

4. The method of claim 3, wherein the leukocytes are neutrophiles or monocytes.

5. The method of claim 1, wherein bone marrow cells or peripheral blood cells are collected from the subject, incubated with the extract in a medium, and returned to the subject.

* * * * *